United States Patent [19]

Jacobsen et al.

[11] Patent Number: 4,521,924
[45] Date of Patent: Jun. 11, 1985

[54] ELECTRICALLY DRIVEN ARTIFICIAL ARM

[75] Inventors: Stephen C. Jacobsen; David F. Knutti; R. Todd Johnson, all of Salt Lake City, Utah

[73] Assignee: University of Utah, Salt Lake City, Utah

[21] Appl. No.: 470,927

[22] Filed: Mar. 1, 1983

[51] Int. Cl.³ .................. A61F 1/00; A61F 1/06
[52] U.S. Cl. ............................. 3/1.1; 3/12.3; 3/12.4
[58] Field of Search ................ 3/1.1, 12-12.8

[56] References Cited

U.S. PATENT DOCUMENTS

| | | | |
|---|---|---|---|
| 1,423,296 | 7/1922 | Armstrong | 3/12.4 |
| 1,475,119 | 11/1923 | Hulsmann et al. | 3/12.4 |
| 2,553,830 | 5/1951 | Motis | 3/12.3 |
| 2,572,914 | 10/1951 | Chapman et al. | 3/12.3 |
| 3,382,506 | 5/1968 | Collins et al. | 3/12.3 |
| 3,491,378 | 1/1978 | Ioffe et al. | 3/1.1 |
| 3,557,387 | 1/1971 | Ohlenbusch et al. | 3/1.1 |
| 3,798,680 | 3/1974 | Prout | 3/12.4 |
| 3,866,246 | 2/1975 | Seamone et al. | 3/1.1 |
| 4,074,367 | 1/1978 | Loveless | 3/1.1 |

Primary Examiner—Ronald L. Frinks
Attorney, Agent, or Firm—B. Deon Criddle

[57] ABSTRACT

A prosthesis for a person with an amputation above the elbow is provided in which elbow motion is provided by an electrical motor contained within the prothesis. Operation of the motor is controlled by electric impulses from selected opposing muscle pairs on the amputee. The prosthesis is constructed with both internal and external modules which are readily replaceable. An electrically operated lock mechanism is provided for locking the elbow motion of the prosthesis. The locking mechanism is controlled by logic circuitry which in turn operates in response to electric impulses from the pair of muscles on the amputee. Novel means are also included which provide passive wrist movement and humeral rotation of the prosthesis. A removable battery module comprising rechargeable storage cells provides power for the motor and the electrically operated lock mechanism.

28 Claims, 15 Drawing Figures

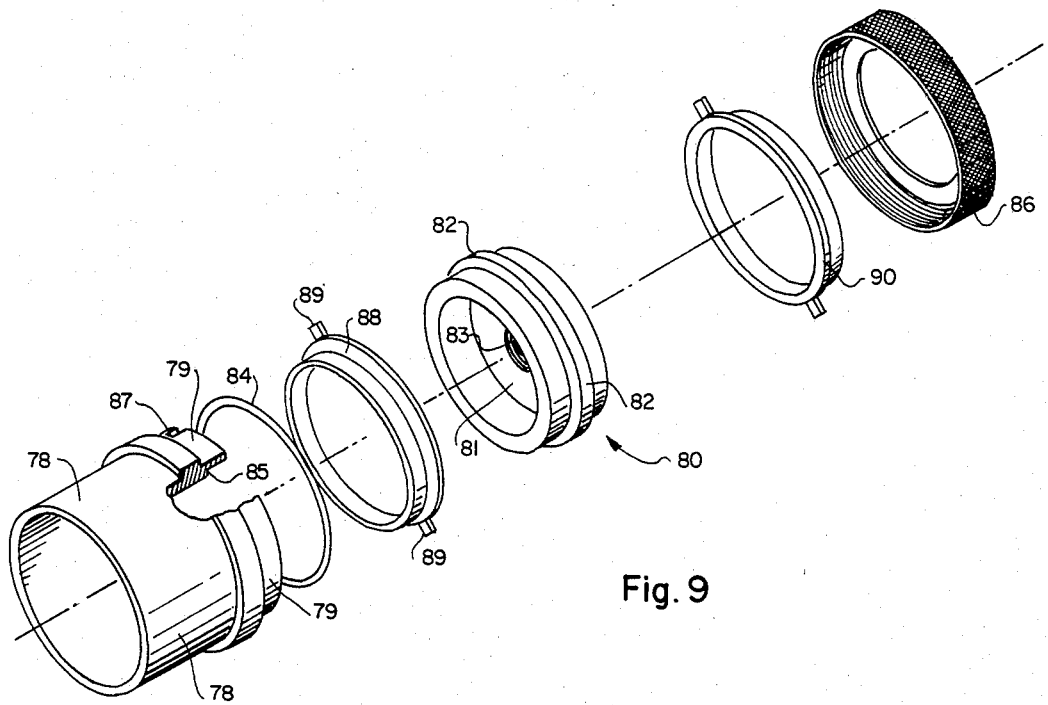
Fig. 9
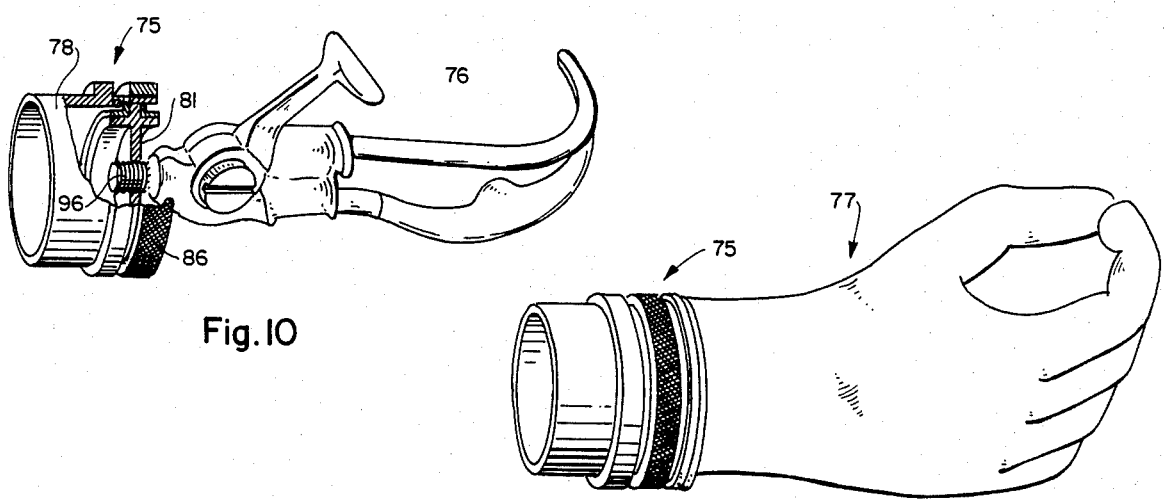
Fig. 10
Fig. 11

ELECTRICALLY DRIVEN ARTIFICIAL ARM

BACKGROUND OF THE INVENTION

1. Field

The invention relates to a prosthesis for use by a person who has an amputation above the elbow.

2. State of the Art

Considerations concerning performance requirements of prosthetic apparatus are exceedingly complex. Various attempts have been made to provide operable prostheses. In conventional artificial arms, a mechanical system is employed with cables connected between the prosthesis and another part of the amputee's body. The amputee operates the prosthesis by pulling the cable by using drastic movements of the portion of the body to which the cables are attached. The movements required to pull the cable are large and unnatural.

The use of electrically driven prostheses has been attempted, and it has been suggested to use biological signals, such as myoelectric impulses from other muscles in the amputee, for control of the electrically driven prostheses. These developments, unfortunately, have not achieved any significant level of success. In many instances systems performed well in laboratory or other controlled environments, but could not withstand the rigors of continued daily use. Further, the electrically driven prostheses which have been devised heretobefore were overly complex, excessive in weight and unnatural in both function and appearance.

3. Objectives

A principal objective of the present invention is to provide a reliable prosthesis which is cosmetically appealing to amputees, is operated electrically to simulate as nearly as possible the elbow action of a natural arm, and is fitable and maintainable by prosthetists in the field. A particular objective of the invention is to provide a prosthesis which is formed of separate but interconnectable modules which can be quickly replaced by a replacement module in the field, with the defective module being transferred to a central facility adapted to rebuild the module. Another objective of the invention is to provide an arm prosthesis which is adapted to swing naturally as the wearer walks and which further moves to the command of the wearer in a natural motion. A still further objective of the invention is to provide an arm prosthesis having an electrically operated elbow locking mechanism which permits the wearer to lift loads that would otherwise exceed the capability of the elbow movement actuator and which also minimizes power consumption of the elbow actuator.

SUMMARY OF THE INVENTION

The above objectives are achieved in accordance with the invention by a prosthesis comprising a number of internal and external modules which provide wrist rotation, elbow flexion and humeral rotation. The arm prosthesis includes a variety of modules designed to selectively replace the functions of the missing joints. Certain joint modules are actuated by passive action while others, especially the elbow module, are operated by an electrical motor contained within the prosthesis. Control of the electrically operated modules utilizes electromyographic signals. The system of interchangeable modules allows the prosthetist to easily assemble a prosthesis which best fits specific amputees in response to the functional needs, available control sites, remnant limb conditions, etc., of the individual amputees. Moreover, the modular system arangement increases the operational availability of the prosthesis, inasmuch as malfunctioning modules can be easily and quickly exchanged in the field, with the malfunctioning modules ultimately being repaired at central facilities for future replacement.

The design of the joint actuators, especially the elbow joint actuation system, permit rapid and graceful movement of the forearm of the prosthesis which contributes to a life-like feel of the prosthesis. The artificial limb of the present invention is made to operate as nearly as possible as a part of the amputee's body, rather than as a stiff and robot-like appendage. The smooth operation of the prosthesis of this invention contributes to a natural appearance as much as the texture and color of the artificial limb.

In the prosthesis of the present invention, a novel, electrically operated locking system is provided for the elbow. The elbow locking system permits the amputee to support static loads in lifting operations which would otherwise exceed the capability of the actuator system for the elbow. The elbow locking system also minimizes power consumption of the elbow actuator system in such situations.

Additional objects and features of the invention will become apparent from the following detailed description, taken together with the accompanying drawings.

THE DRAWINGS

A particular embodiment of the present invention representing the best mode presently contemplated of carrying out the invention is illustrated in the accompanying drawings, in which:

FIG. 9 is an exploded pictorial of the wrist connection mechanism of the prosthesis of FIG. 1;

FIG. 10 is a pictorial of a hook member attached to the assembled wrist connection mechanism of FIG. 9;

FIG. 11 is a pictorial of an artificial hand member attached to the assembled wrist connection mechanism of FIG. 9.

DETAILED DESCRIPTION OF THE PREFERRED EMBODIMENT

Figure 1:
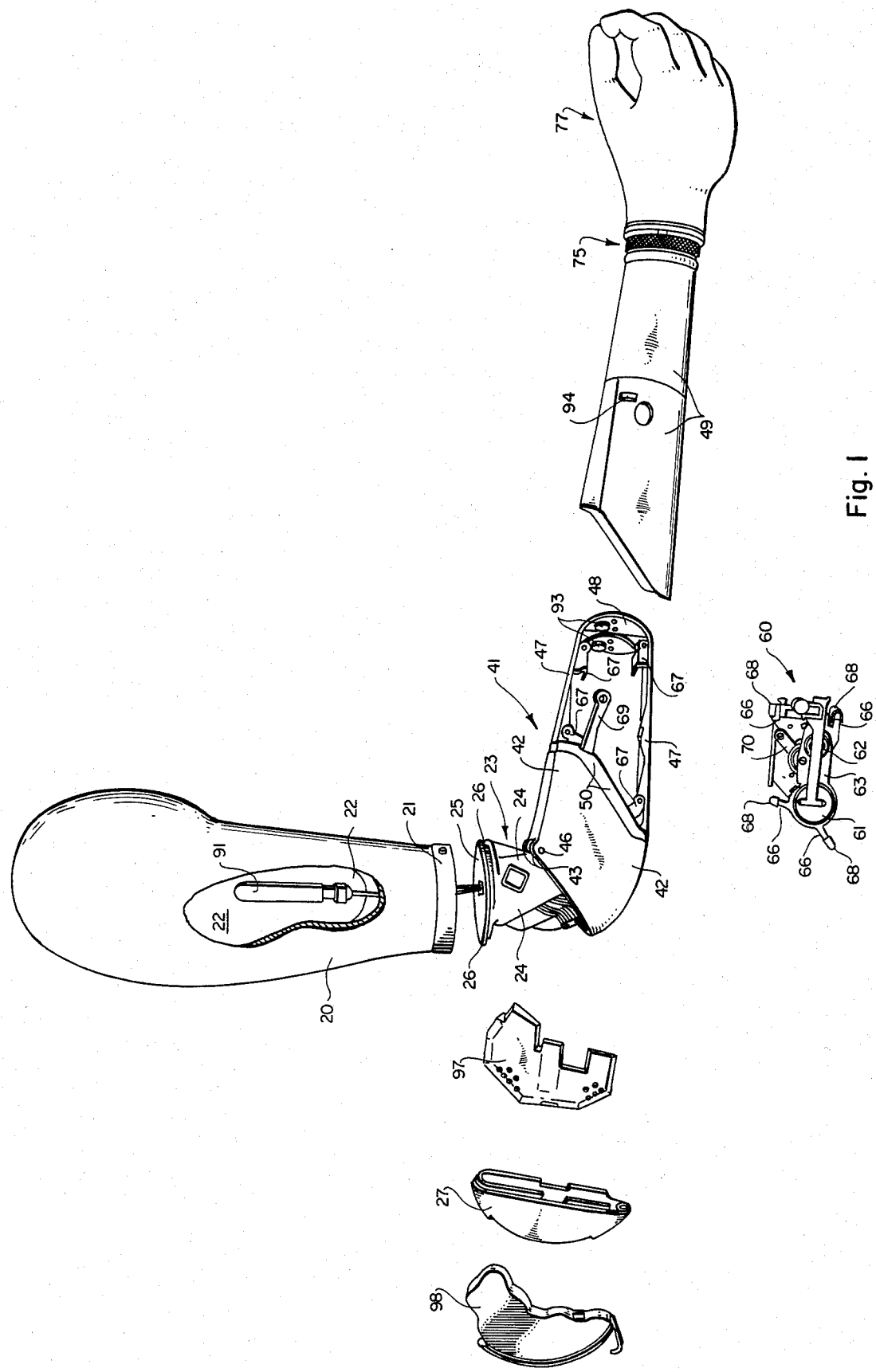
FIG. 1 is a partially exploded pictorial of an arm prosthesis in accordance with the invention.

The present invention relates to prosthetic devices for a person with an amputation above the elbow. If the amputee has some arm remnant left above the elbow, the prosthesis of this invention can be attached to the remnant using conventional socket/harness techniques. For amputees whose arms have been amputated past the shoulder, a harness system as is known in the art is used to attach the prosthesis to the amputee.

As illustrated in the drawings, an upper arm or socket module is provided which is adapted to be attached to the remnant of the amputee's upper arm or the shoulder portion of the amputee's torso. The socket module comprises an outer member 20 which extends from the humeral rotation unit 21 up to the shoulder area. An internal socket member 22 is fitted within the external socket member 20. The internal socket member 22 extends inside the outer socket member 20 a distance depending on the shape and size of the remnant limb of the amputee, with the internal socket member 22 further being adapted to make a uniform contact and glove-like fit with the remnant limb.

An elbow module 23 is attached to the humeral rotation unit 21 at the lower end of the socket module. The elbow module comprises a hollowed out central body portion 24 which has a substantially flat upper end 25. The outer perimeter of the flat upper end 25 is substantially circular and is formed into an annular flange 26. Downwardly extending forward and side walls are integrally molded to the upper end 25 and to themselves to form the hollowed out central body portion 24 of the elbow module. A removable rear cap member 27 (FIGS. 1 and 2) is attached to the backside of the elbow module so as to essentially form an enclosed hollow cavity within the hollowed out elbow module.

The elbow module 23 is connected to the socket module so that the elbow module 23 can be rotated relative to the socket module about the longitudinal axis of the socket module. The means for connecting the elbow module to the socket module as illustrated comprises the humeral rotation unit 21 in combination with the flat upper end 25 of the body portion 24 of the elbow module. The humeral rotation unit, as shown in exploded, pictorial relationship in FIG. 2, comprises an annular fitting 28 which is adapted to be attached to the lower end of the outer socket member 20. Advantageously the lower end of the outer socket member 20 is molded in situ about the knurled upper end portion 30 of the annular fitting 28. A flat abutment ring 29 is formed about the annular fitting 28 adjacent to or near the inside edge of the knurled portion 30, and the end of the socket member is molded so as to abut against the upper side of the ring 29.

The annular fitting 28 further comprises a cylindrical end portion 31 which extends away from the end of the outer socket member 20 of the socket module. The cylindrical end portion 31 has a substantially flat, circular end face 32, and the cylindrical end portion 31 is substantially coaxial with the longitudinal axis of the outer socket member 20 of the socket module. A circumferential flange or ring 33 extends around the cylindrical end portion 31 adjacent to but spaced slightly from the flat end face 32 (see FIG. 2a) of the annular fitting 28.

An annular friction band 35 is provided which has an annular recess 34 formed around the inside surface at one end portion of the friction band 35. The annular friction band 35 is adapted to fit around the cylindrical end portion 31 of the annular fitting 28, with the annular recess 34 in the friction band 35 being adapted to engage or receive therewith the circumferential flange or ring 33 on the annular fitting 28. The other end portion of the friction band 35 is adapted for attachment to the upper end of the elbow module 23 to hold the flat upper end 25 of the elbow module 23 in parallel, closely spaced relationship with the flat, circular end face 32 of the annular fitting 28. As shown in the illustrated embodiment, the friction band 35 has a longitudinal dimension somewhat greater than the longitudinal length of the cylindrical end portion 31 of the annular fitting 28, so that when the friction band 35 is in place on the cylindrical end portion 31 of the annular fitting 28, the lower or other end portion of the friction band 35 extends outwardly from the end face 32 of the cylindrical end portion 31 of the annular fitting 28. The lower extending portion of the friction band 35 is adapted to fit over the annular flange 26 of the flat upper end 25 of the elbow module 23. As illustrated, a second annular recess 36 is formed around the inside surface of the friction band 35 at the other end portion thereof. The second annular recess 36 is adapted to engage or receive therewithin the annular flange 26 of the flat upper end 25 of the elbow module 23.

An adjustable tension band 37 is adapted to encircle the friction band 35 and provide adjustable compression of the friction band 35. In the preferred illustrated embodiment, the friction band 35 is split or broken so as to not have a continuous perimeter. When in place on the cylindrical end portion 31 and annular flange 26 of the elbow module 23, the friction band 35 is expanded slightly so that the split or broken ends are slightly spaced apart. The adjustable tension band 37 fits around the perimeter of the friction band 35, and the tension band 37 is adapted to be tightened around the friction band 35. The friction band 35 can have end flanges, as illustrated, which form a groove in which the tension band 37 is received.

In the illustrated embodiment a tension transmission band 38 is provided between the friction band 35 and the tension band 37. The band 38 permits uniform application of tension to the friction band 35. As the tension band 37 is tightened, the tension is transmitted through the transmission band 38 to increase frictional movement of the friction band 35 relative to the cylindrical end portion 31 of the annular fitting 28. The transmission band 38 further inhibits and essentially eliminates relative movement between the tension band 37 and the friction band 35.

The friction band 35 is adapted to frictionally slide about the cylindrical end portion 31 of the annular fitting 28. The movement can be adjusted from relatively free movement to a locked conditon in which movement is completely restrained simply by adjusting the tension band 37. Movement between the friction band 35 and the flat upper end 25 of the elbow module 23 is not necesary, and in the preferred illustrated embodiment, such movement is prevented. This is done by providing a filled in or discontinuous area 39 in the second annular recess 36 of the friction band 35 and a corresponding notch 40 in the annular flange 26 at the flat upper end 25 of the elbow module 23. The filled in area 39 is received within the notch in the flange 26 as the flange 26 is in turn received within the annular recess 36. The engagement of the filled in area 39 in the notch 40 of the annular flange 26 prevents relative movement between the friction band 35 and the flat upper end 25 of the elbow module 23.

The tensioning of the tension band 37 is accomplished by providing a split or broken section in the tension band 37 such that the tension band 37 does not have a continuous perimeter. A tension screw (not illustrated) is provided which fits through a bore in one of the split ends of the tension band 37 and is threaded into an internally threaded bore in the other split end of the tension band 37. As the tension screw is advanced in the threaded bore, the split ends of the tension band are forced together to increase the force or tension exerted through the transmission band 38 to the friction band 35.

The circumferentially tensioned connecting means as illustrated and described above provides easy disconnect capability between the elbow module 23 and the outer socket member 20 in addition to the adjustable friction movement discussed above. The connecting means is exoskeletal for load diffusion. An opening (not shown) in the center of the connecting means allows convenient electrical interconnection between the elbow module and the socket module for purposes which will be more fully discussed hereinafter. The annular fitting 28, and the tension band 37 of the connecting means are preferably made of metal such as aluminum or stainless steel. The friction band 35 is made of an organic polymeric material such as nylon, polyester, polypropylene, polyethylene, etc. The transmission band 38 can be made of an organic polymer, and is preferably made of an elastomeric polymer impregnated in a fabric material.

Figure 2:
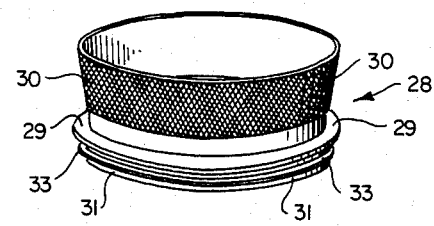
FIG. 2 is an exploded pictorial of the passive humeral rotation mechanism associated with the elbow module of the prosthesis shown in FIG. 1.
Figure 2:
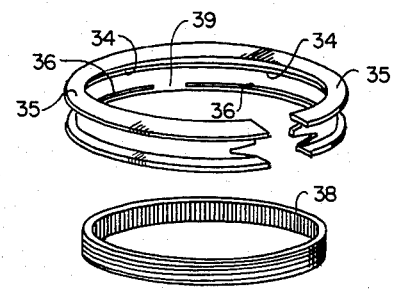
Figure 2:
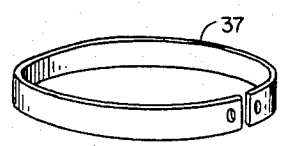
Figure 2:
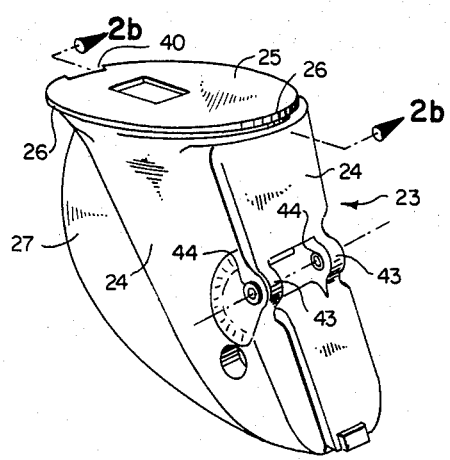
Figure 2A:
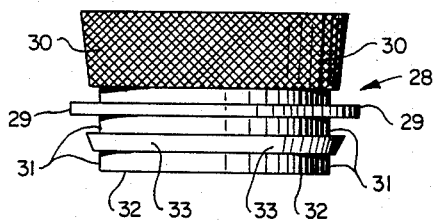
FIG. 2a is an elevation view of the annular fitting member of the humeral rotation mechanism of FIG. 2.

A forearm module, shown generally by the reference numeral 41 in FIG. 1, is hingedly attached to the elbow module 23. The forearm module comprises a hinged member 42 which is adapted to be pivotally attached to the elbow module 23. As best shown in FIG. 2, the elbow module 23 has an opening in the front of the central body portion 24 thereof. The opening extends between the two sides of the body portion 24, with reinforced hubs 43 being formed at the opposite ends of the opening in the respective sides of the body portion 24. Brass journal bearings 44 are centered in and extend through the hubs 43, with the journal bearings 44 being aligned in a straight line with each other.

The back portion of the hinged member 42 is formed by sidewalls which enclose a substantially hollow chamber thereat. The chamber is enclosed at the forward end of the hollow back portion by a forward wall 45 (FIG. 3) which is about midway along the length of the hinged member 42. The back end of the chamber formed by the sidewalls is open for pivotally receiving the elbow module 23 within the chamber at the back portion of the hinged member 42. The top back edge of the hinged member 42 is provided with hinge means which mates with the hubs 43 on the elbow module 23 such that the hinged member 42 is hingedly attached to the elbow module 23 for pivotal movement about a hinge pin 46 extending through the journal bearings 44 in the hubs 43 of the elbow module 23.

The forward portion of the hinged member 42 is formed of a substantially open framework. The framework comprises elongate support members 47 extending forwardly from the top and bottom edges of the hollow chamber portion of the hinged member 42. A substantially circular end disc 48 is attached to the forward extending ends of the support members 47. An elongate forearm cover member 49 is provided to slide over the framework portion of the hinged member 42. The forearm cover member 49 is substantially tubular and is open at both ends. The back end of the forearm cover member 49 is shaped to mate with the forward portion of the hollow chamber section of the hinged member 42. For purposes of making a smooth connection, the forward edges of the sidewalls of the hollow chamber section of the hinged member 42 are indented or recessed as shown generally by the numeral 50 in the drawings. The back end of the forearm cover member 49 is shaped so as to fit telescopically over the recessed portion 50 of the hinged member 42, and means are provided for securely attaching the forearm cover member 49 to the hinged member 42. The combined cover member 49 and hinged member 42 have the general shape of a human forearm.

As mentioned previously, the enclosed back portion or hollow chamber section of the hinged member 42 has an open end at the end which is pivotally connected to the elbow module 23 so that the elbow module can be received within the hollow chamber section of the hinged member 42 when the hinged member 42 is pivoted about its attachment to the elbow module 23. The elbow module 23 is shaped so as to be neatly received within the hollow chamber section of the hinged member 42 in such a manner that there is essentially no open gap formed between the elbow module 23 and the hinged member 42 during the entire movement of the forearm module 41.

Figure 2B:
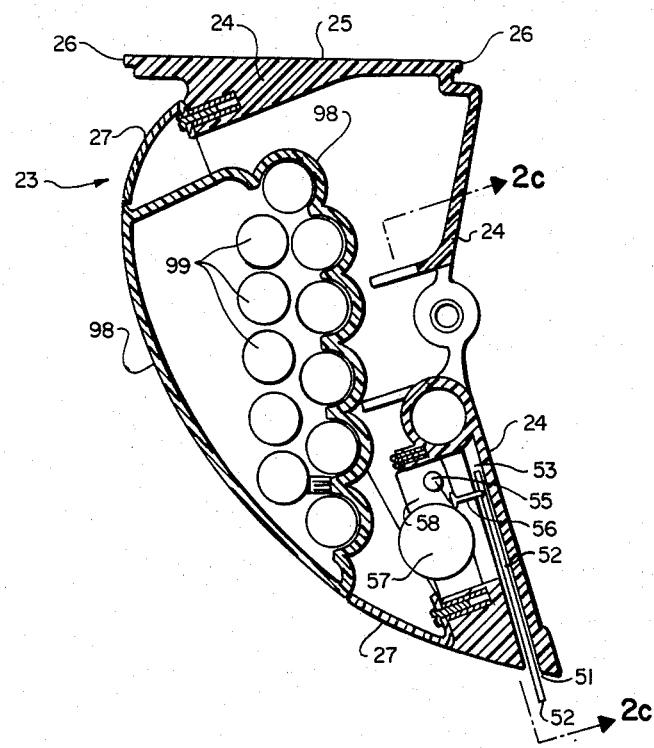
FIG. 2b is a vertical cross section through the elbow module taken along line 2b-2b of FIG. 2.

Novel means are provided for locking the forearm module 41 in place with respect to the elbow module 23 at various positions in the movement of the forearm module 41 relative to the elbow module 23. The locking means comprises a slot opening 51 in the lower end of the elbow module 23 (FIG. 2b). The slot opening 51 is located adjacent to the forward wall of the central body portion 24 of the elbow module 23. An elongate pin or slide bar 52 is positioned within the opening 51 and is adapted to move longitudinally within the opening 51. A pair of guide ribs 53 are positioned within the inside of the forward wall of the central body portion 24 of the elbow module 23 on opposite sides of the opening 51. The guide ribs 53 and the inside surface of the forward wall form a slot in which the slide bar 52 is adapted to move back and forth therein.

Figure 2C:
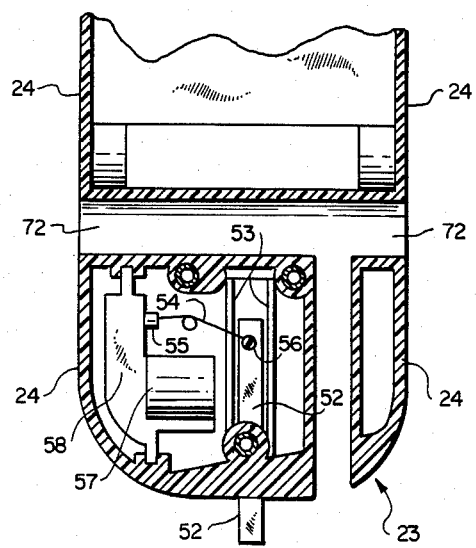
FIG. 2c is a partial cross section through the elbow module taken along line 2c-2c of FIG. 2b.

Means are provided for moving the locking pin or bar 52 back and forth in the opening 51 and the slot formed by the guide ribs 53 between an extended position in which the end of the locking pin or bar 52 extends outwardly from the opening 51 and a retracted position in which the end of the locking pin or bar 52 is retracted so as to not extend outwardly from the opening 51. As best shown in FIGS. 2b and 2c and in isolation in FIG. 4, the preferred means for moving the locking pin or bar 52 comprises a wire spring 54 which is cantilevered at its one end to a rotatable base 55, with the other end of the spring 54 being adapted to contact or make engagement with the locking pin or bar 52. Advantageously, the end of the spring 54 engages a set screw means 56 in the pin or bar 52. As will become evident from the following discussion, the spring 54 must be able to turn about its longitudinal axis at its engagement to the pin or bar 52. Thus, it is preferable that the end of the spring 54 engages an opening or bore in the set screw means 56 such that the end of the spring 54 is free to rotate therein. The spring 54 is biased at an angle to the rotatable base 55, and means are provided for rotating the base 55 from a first position through an angle of about 180 degrees to a second position and vice versa about an axis coincident with the attachment of the spring 54 to the base 55. When the base is in its first position, the spring 54 biases the locking pin or bar 52 to slide downwardly such that the end of the pin or bar 52 extends from the opening 51. By rotating the base 180 degrees to its second position, the spring 54 is turned over and biases the pin or bar 52 to withdraw to its retracted position within the elbow module 23. A small electric DC motor 57 and a gear mechanism 58 is provided which is adapted to very rapidly rotate the rotatable base 55 between its two positions. Means are provided as explained hereinafter for operating the DC motor to move the locking pin or bar 52.

Figure 3:
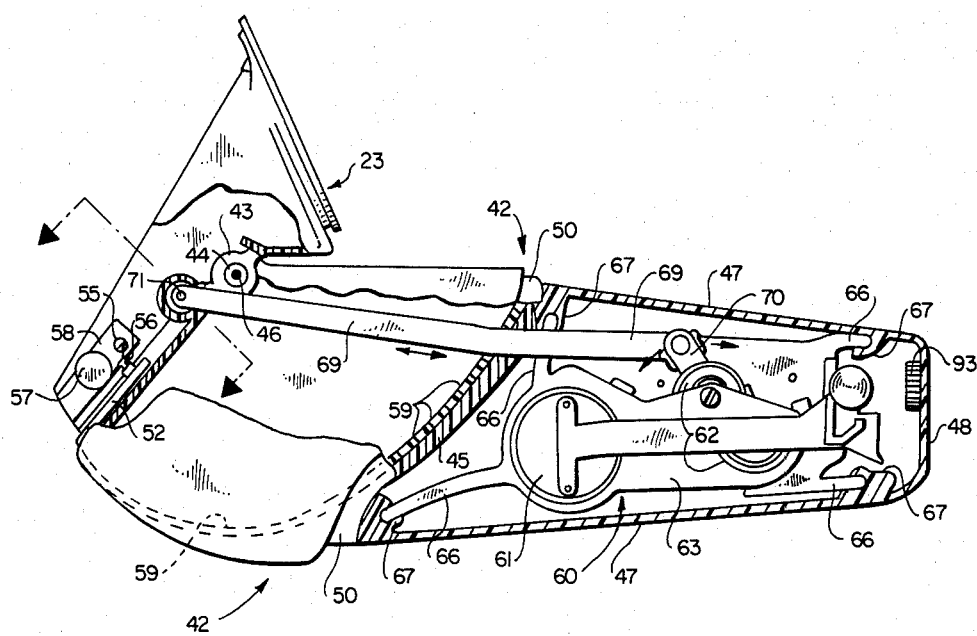
FIG. 3 is an elevation of the upper forearm module and the elbow module of the prosthesis shown in FIG. 1, with the modules being shown partially broken away to illustrate the drive mechanism for the elbow movement.
Figure 4:
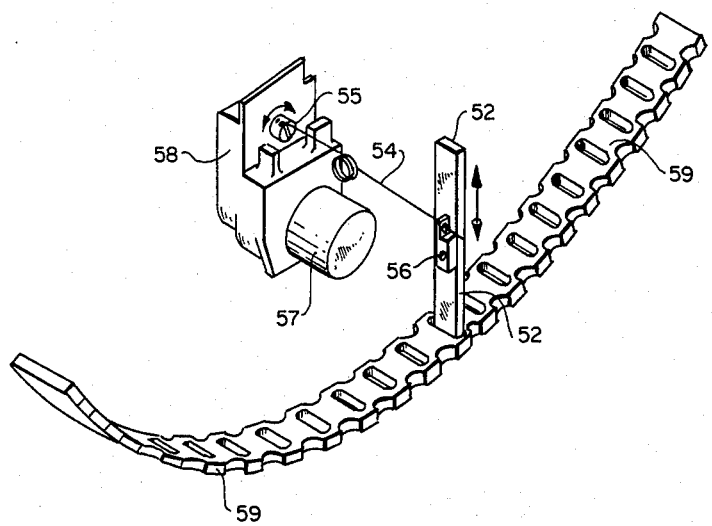
FIG. 4 is a pictorial view of the elbow locking mechanism which has been isolated from the prosthesis of FIG. 1.

The means for locking the forearm module 41 in place with respect to the elbow module 23 further comprises a curved lock member 59 which is firmly attached to the inside surface of the hollow back portion or hollow chamber section of the hinged member 42. The lock member 59, as best shown in FIG. 4, has a plurality of detent holes equally spaced along the length thereof. As shown in FIG. 3, the lock member 59 is positioned along the inside surface of the hinged member 42 so that as the hinged member 42 pivots about its attachment to the elbow module 23, the curved elongate lock member 59 moves in an arc such that the detent holes therein move successively back and forth directly beneath the opening in the elbow module 23. Thus, by activating the lock pin or slide bar 52 to extend from the opening 51 in the elbow module 23, the pin or bar 52 will engage one of the detent holes in the lock member 59 to lock the forearm module 41 in place with respect to the elbow module 23. The forearm module 41 can, thus, be locked in place at various positions in its movement relative to the elbow module 23. The curved lock member 59 is preferably insert-molded into the inside surface of the hollow back portion or hollow chamber section of the hinged member 42.

A motorized drive module 60 is provided for imparting pivotal movement of the forearm module 41 relative to the elbow module 23. The drive module comprises a DC motor 61 and gear reduction transmission 62 mounted on a frame 63 which is adapted to be removably attached to the hinged member 42 within the open framework formed by the support members 47 and end disc 48 of the hinged member 42. The motor 61 is a Micromo cylindrically wound DC motor. The reduction transmission 62 has a ratio of 323 to 1 and is implemented by a first stage reduction utilizing a low noise timing belt drive 64 and two subsequent stages of high efficiency Evoloid, high lead, hellical gearing 65.

The motor 61 and transmission system 62 are mounted within a frame 63 which as mentioned previously is removably attached to the hinged member 42 within the open framework at the forward end of the hinged member 42. In the preferred, illustrated embodiment, the frame 63 has four leg members 66 which extend outwardly from the four corners of the frame 63. The ends of the leg members 66 are received in cavities or slots 67 molded into the support members 47 of the open framework at the forward end of the hinged member 42. The cavities or slots 67 are preferably closed at mutually respective ends thereof, and the ends of the leg members 66 are received within the cavities or slots 67 so as to abut against the closed ends thereof. Removable end caps (not illustrated) are secured at the other ends of the cavities or slots 67 to securely hold the ends of the leg members 66 in place. Rubber end cap insulators 68 can be provided at the ends of the leg members 66 to make a compression fit of the ends of the leg members 66 within the cavities or slots 67. In addition, the rubber end caps 66 dampen vibration and acoustic noise from the motor 61 and transmission system.

The transmission system 62 drives a linkage coupler member 69 which transmits rotary motion from the motor 61 and transmission system 62 to the elbow module 23. The forward end of the linkage member 69 is connected to a drive lever 70 which is in turn connected to the transmission system 62. As the motor 61 is actuated, the transmission system moves the drive lever 70 in pivotal movement, and the drive lever 70, in turn, imparts reciprocating, longitudinal movement to the linkage member 69.

Figure 5:
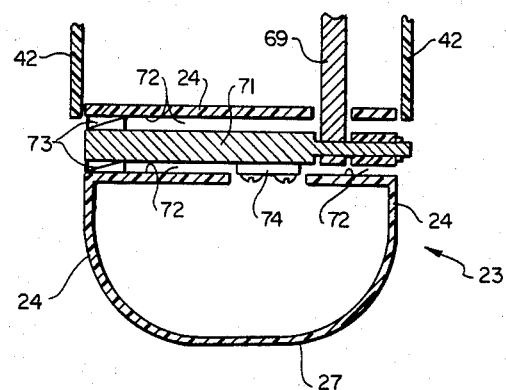
FIG. 5 is a cross section through the pivot axis of the elbow showing the strain guage associated therewith.

The other end of the linkage coupler member 69 is connected to a transversely cantilevered strain guage, force transmitting member 71 best shown in FIG. 5. The force transmitting member 71 is positioned within an elongate opening 72 through the elbow module 23. The opening 72 is shown in FIGS. 2, 2b, and 2c without the force transmitting member 71 positioned therein. The force transmitting member 71 is shown in position within the opening 72 in FIGS. 3 and 5. One end of the force transmitting member 71 is firmly and securely attached, such as by an enlarged compression fitting 73, to the elbow module 23 at one end of the opening 72. The force transmitting member 71 is positioned coaxially within the opening 72 and the linkage coupler member 69 is attached in journal fashion to the other end portion of the force transmitting member 71. As the linkage member 69 moves to and fro, it exerts a force on the force transmitting member 71 which in turn transmits the force to the elbow module 23. The force transmitting member 71 has a strain guage 74 associated therewith. The strain guage 74 measures elbow torque exerted by the linkage member 69 independently of the postion of the elbow module 23 relative to the forearm module 41. The strain guage 74 is utilized in controlling the locking mechanism as will be described more fully hereinafter.

To complete the exterior portions of the prosthesis, a wrist module 75 is attached to the forward end of the forearm cover member 49. The wrist module 75 is adapted to have a hook 76 or simulated hand 77 removably attached thereto. Although not shown in the drawings, the hook 76 and the simulated hand 77 can be operated by external cables which are attached to the wearer as is well known in the art of prosthetic arms.

The wrist module 75 includes means for manually rotating and adjusting the hook 76 or simulated hand 77 relative to the forearm module 41 about the longitudinal axis of the forearm module 41. In the preferred illustrated embodiment, the wrist module 75, as shown in exploded pictorial arrangement in FIG. 9 comprises a substantially cylindrical attachment member 78 having external threads 79 at one end thereof, with the other end of the attachment member 78 having adapted to be secured to the forward end of the forearm cover 49. Preferably, the forward end of the forearm cover 49 is cylindrical having a substantially circular cross section. The other end of the attachment member 78 is circular in cross section and adapted to be received coaxially in firm engagement with the forward end of the forearm cover 49. The attachment member 78 can be cemented within the forward end of the forearm cover 49 to insure secure attachment. The forward end of the forearm cover 49 can be cut off at various lengths so that the forearm module 41 approximates the length of the amputated forearm of the person who is to wear the prosthesis.

Returning to the construction of the wrist module 75, an insert member 80 is provided comprising a cylindrical body which is open at one end and has an end cap 81 at the other end thereof. Further, the cylindrical body of the insert member 80 has a raised band 82 circumscribing the central portion thereof, with the diameter of the raised band 82 being of such size that the insert member 80 with the raised band 82 is adapted to fit coaxially within the one end of the cylindrical attachment member 78. The end cap 81 of the insert member 80 has a bore 83 therethrough which is coaxial with the cylindrical body of the insert member 80. The bore 83 is adapted to receive attachment means for a hook or simulated hand for attachment to the insert member. Preferably, the bore 83 is threaded so as to be adapted to receive a threaded stud 96 of a hook or simulated hand. FIG. 10 is cut away to show the threaded stud 96 of a hook 76 threaded securely into the bore 83 of the end cap 81.

An elastomeric O-ring 84 is adapted to fit circumferentially around the cylindrical body of the insert member 80 between the one end of the cylindrical body and the raised band 82 on the cylindrical body. Abutment means are provided in the interior of the cylindrical attachment member 78. The abutment means comprises an annular shoulder or circumferential lip 85 on the inside surface of the cylindrical attachment member 78 (FIG. 9). The shoulder or lip 85 is spaced inwardly from the one end of the attachment member 78. The abutment means, i.e. the shoulder or lip 85 is adapted to fit over the cylindrical body of the insert member 80 and to abut the O-ring 84 when the one end of the insert member 80 is fit within the attachment member 78. The O-ring 84 is, thus, constrained between the raised band 82 on the insert member 80 and the abutment means as the insert member 80 is moved toward the abutment means.

A screw ring 86 is adapted to be threaded on the external threads of the cylindrical attachment member 78 and to advance the insert member 80 toward the abutment means within the cylindrical attachment member 78 as the screw ring 86 is advanced on the threads of the attachment member 78. The O-ring 84 is thereby compressed between the abutment means, the raised band 82, the cylindrical body of the insert member 80 and the interior surface of the cylindrical attachment member 78 to progressively inhibit rotational movement of the insert member 80 relative to the attachment member 78 as the screw ring 86 is advanced on the threads of the attachment member 78.

In the preferred embodiment as illustrated in FIG. 9, at least one longitudnal keyway 87 is provided extending from the one end of the cylindrical attachment member 78 substantially to the abutment means, i.e., to the shoulder or lip 85 on the inside surface of the cylindrical attachment member 78. Advantageously, two keyways 87 are provided spaced 180 degrees from each other. A bearing ring 88 made of a polymeric material is adapted to fit within the cylindrical attachment member 78, with one end of the bearing ring 88 abutting the shoulder or lip 85 on the inside surface of the cylindrical attachment member 78. The bearing ring 88 has a number of ears or keys 89 equal to the number of keyways 87 in the cylindrical attachment member 78, with the keys 89, which extend from the outer periphery of the bearing ring 88, being adapted to be received in the corresponding keyways 87 in the cylindrical attachment member 78. Because of the interlocking keys 89 and keyways 87, the bearing ring 88 is secured firmly from movement with respect to the cylindrical attachment member 78. In the embodiment employing the bearing ring 88, the O-ring 84 abuts the bearing ring 88 when the O-ring 84 and insert member 80 are positioned in the cylindrical attachment member 78.

In the preferred embodiment as illustrated, a second bearing ring 90, which is made of a polymeric material, is adapted to fit between the insert member 80 and the screw ring 86. The screw ring 86 then presses against the second bearing ring 90, and the second bearing ring 90 in turn presses against the insert member 80 when the screw ring is advanced on the threads of the cylindrical attachment member 78.

Control of elbow flexion, i.e., movement of the forearm module 41 relative to the elbow module 23, and control of the locking mechanism are achieved by an electrical control system which utilizes cutaneously measured electromyographic signals from two antagonist muscles on the stump or torso of the amputee. Generally, remnants of biceps and triceps muscles are used; however, in certain situations involving dysfunction or loss of these muscles, anterior and posterior deltoids can be used, as well as other sets of antagonist muscles.

The electromyographic signals are monitored by skin electrodes 91 which are placed in contact with the antagonist muscles. As illustrated, the skin electrodes 91 are located on the internal socket member 22 for prosthetic arms to be used by those amputees which have a remnant of the upper arm below the shoulder. The skin electrodes are mounted on the socket member 22 in such manner that the actual electrode extends through an opening in the socket member to make contact with the desired muscle. The electromyographic signals detected by the skin electrodes 91 are monitored by high performance preamplifiers located in a common housing with the skin electrodes directly over each muscle site. For electrical noise rejection, the electromyographic signals, as monitored by the preamplifiers, are processed by two band-pass filters with a third order low frequency roll-off at 50 Hz and a second order high frequency roll-off at 1,000 Hz.

Figure 12:
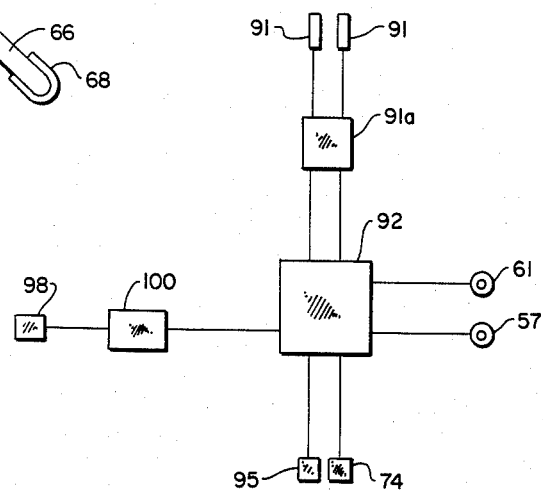
FIG. 12 is a block diagram of the electrical control system of the prosthesis of FIG. 1.

A block diagram of the control system is shown in FIG. 12. As mentioned above, the electromyographic signals from the electrodes 91 are monitored by the preamplifiers which are identified in FIG. 12 by the reference numeral 91a. The signals from the preamplifiers 91a are sent to a controller 92 where after full wave rectification, the signals are differenced to provide a command signal. The command signal is then processed by the controller 92 through a low pass, nonlinear, adaptive filter which adjusts its time constant via a function whose input is the smoothed time-rate-of-change of the command signal. Basically, the adaptive filter maintains a long time constant (about 500 milliseconds) when the absolute value of the command signal derivative is low. This allows stable manipulations to occur without noise-induced "jitter", i.e., high signal-noise ratio, at the expense of rise time. When rapid motions are required by the amputee, the command signal derivative increases and the filter time constant is suppressed to a minimum of about 50 milliseconds, i.e., faster rise time with less suppression of noise.

The command signal which has been processed through the adaptive filter is then sent to a high frequency pulse width modulated amplifier. The output of this amplifier is used to power the motor 61 of the motorized drive module 60. A pair of potentiometers 93 are provided for adjusting the gains in the output of the pulse width modulated amplifier. The potentiometers 93 are mounted on the end disc 48 of the framework structure of the forward portion of the forearm module 42. Access openings 94 are provided on opposite sides of the forearm cover plate 49 so that the potentiometers 93 can be adjusted by the amputee to modify the "feel" of the prosthesis. A number of internal adjustments in the controller can be provided to modify time constants, dead bands, and gains. The internal adjustments permit fine tuning of the controller operation.

The motorized drive module 60 is designed to be capable of providing torques sufficient to permit the manipulation of loads up to about 4 or 5 pounds, with speed which allow full joint excursions in less than about 0.75 seconds. The motor 61 and gear reduction transmission 62 are backdrivable to prevent damage to the transmission system. In addition, low mechanical output impedance of the motorized drive module is provided such that graceful, free-swing operation of the prosthesis is achieved which results in a more natural feel to the amputee.

For lifting demands which exceed the capability of the motorized drive module 60 and for the minimization of power consumption, the elbow module 23 can be actively locked in various positions relative to the forearm module 41 as described hereinbefore. The elbow locking control can be provided by particular behaviour of the two antagonist electromyographic signals which are also used in controlling the elbow flexion or by a third signal obtained from a skeletal motion (shoulder) switch or by the electromyographic activity of another selected muscle. In the preferred, illustrated embodiment of the prosthesis of this invention, the elbow locking control is provided by monitoring particular behaviour of the electromyographic signals which are also used in operating the motor 61 of the motorized drive module 60. Operation of the locking mechanism in such a manner is convenient and relatively natural for the amputee, requiring no other signals or body motions from the amputee.

To engage the motor 57 which in turn activates the lock member 59 of the elbow locking mechanism, the amputee simply holds the elbow steady, i.e., angular velocity of the forearm module 41 relative to the elbow module is held close to zero. The controller 92 monitors the angular velocity of forearm module 41 by a signal generator associated with the motorized drive module 60. The signal generator advantageously comprises a Micromo tachometer 95 which is mounted in the frame 63 of the motorized drive module 60 and is driven by a belt from the transmission system 62 or motor 61. The tachometer 95 is in simple terms an alternator which produces an electric signal when driven by the belt from the transmission system 62 or motor 61. As shown diagrammatically in FIG. 2, the signal from the tachometer is sent to the controller 92. The controller 92 also monitors the elbow torque as indicated by the output signal of the strain guage 74 associated with mechanism for transferring the force from the linkage coupler member 69 to the elbow module 23.

If, during the period in which the amputee holds the elbow steady, the elbow torque is simultaneously monitored as being above a preset threshold, the controller activates the motor 57 on the locking mechanism to move the pin or slide bar 52 into locking engagement with the lock member 59. The controller incorporates a time function into the activation of the locking mechanism. In particular, the elbow torque must be monitored above the preset threshold for a specified time interval before the controller 92 activates the motor 57. A maximum time interval of approximately 0.75 seconds is required by the controller 92 when the elbow torque is just above the threshold. The time internal is reduced to approximately 0.4 seconds when the elbow torque is close to the maximum capability of the motorized drive module 60. Inasmuch as the motorized drive module 60 is not active when the lock mechanism is engaged, the activation system for the drive module 60 is transferred to an inactive "sleep" mode so as to minimize power consumption.

Unlocking of the locking mechanism occurs when the amputee rapidly co-contracts the antagonist muscles and subsequently relaxes below a low threshold within a specified time interval. When the sum of the electromyographic signals from the antagonist muscles is above the saturation level of the amplifier for each of the signals, and then subsequently are reduced below the threshold within a specified time interval, the controller 92 activates the motor 57 to retract the pin or slide bar 52 from engagement with the lock member 59. The "contract-relax" sequence is the only part of the lock-unlock system which is without an obvious correlative in the natural movement of a person's arm. Such a sequence, however, has several advantages. First, the amputee must contract both antagonist muscles simultaneously and in fairly rapid manner to unlock the elbow locking mechanism, thereby making unintentional locking and unlocking less likely. Second, no other control site or activity is required to unlock the elbow. Third, the contract-relax sequence leaves the amputee with low electromyographic signals from the antagonist muscles which avoids "jumping" of the forearm when the locking mechanism is released.

It should be recognized, however, that other methods can be utilized to lock and unlock the locking mechanism. For example, control of the locking mechanism can be achieved using a third or separate signal to the controller. In such a case, either a shoulder-operated switch, or a well controlled electromyographic signal from another muscle of the amputee can be used to cause the elbow lock mechanism is sequentially lock and unlock as each signal is received by the controller.

The locking mechanism of the present invention is specifically designed to prevent catastrophic unloading of the prosthesis when the locking mechanism is released or unlocked. When the locking system receives an unlock command from the controller, the motor 57 and gear mechanism 58 rotates the rotatable base 55 and wire spring 54 so that the pin or slide bar 52 is biased to retract from the lock member 59, and the pin or slide bar 52 will retract and unlock the elbow when shear loading on the pin or slide bar 52 is sufficiently reduced to allow the pin or slide bar 52 to slide away from the lock member 59. However, if the arm, is actually supporting a significant load when the locking mechanism is activated to unlock the elbow, the shear forces between the pin or slide bar 52 and the lock member 59 prevent withdrawal of the pin or slide bar 52.

The electronic controller 92 is preferably mounted within the hollow cavity within the elbow module 23, with the cap member 27 of the elbow module 23 being removable so as to provide access to the cavity and the electronic controller mounted therewithin. Preferably, the electronic components of the controller are mounted within a pair of removable modules 97 (FIG. 1) which are adapted to fit along opposite sides of the cavity formed within the elbow module 23.

Power for operating the electronic controller 92 and the motors of the drive module 60 and the elbow locking mechanism is provided from a battery pack module 98 (FIGS. 1 and 2b) which is also mounted within the cavity in the elbow module 23, with the battery pack module 98 being adapted to be removably received within the cavity in the elbow module 23 through an opening within the elbow module 23. Preferably, an opening is provided in the cap member 27 of the elbow module 23, with the battery pack module 98 being of such a shape that the outer end face thereof forms a continuous surface which closes the opening in the cap member 27 when the battery pack module is positioned within the cavity in the elbow module 23. The battery pack module 98 itself contains a plurality of rechargeable cells 99 which are wired in series within the module 98. Preferably, the battery pack module 98 contains ten 450 milliamps hour, rechargeable, nickel-cadmium cells 99 which provide an output voltage of about 12 volts. The battery pack module 98 is shaped to efficiently fit within and utilize the available space within the elbow module 23. The trailing end of the battery pack module 98 forms a smooth closure for the battery pack opening in the cap member 27, and the cap member 27 and the trailing end portion of the battery pack module 98 blend with and form part of the external contour of the elbow module 23. The inner side of the battery pack module has an opening therein with exposed contacts to the bank of batteries. When inserted within the elbow module 23, the contacts are adapted to engage corresponding contacts within the elbow module 23 which in turn feed electrical current from the bank of batteries to the electrical components of the prosthesis. The battery pack module 98 is readily removable from the elbow module for recharging of the batteries. The fully charged battery pack is designed to provide for at least one day's operation of the prosthesis.

Preferably, a controlled reference power control circuit, as is well known in electrical circuit art, is provided to isolate the controller circuitry from load-induced voltage fluctuations. The power control circuit is shown diagrammatically in FIG. 12 by the reference numeral 100. In actuality, the power control circuit is advantageously included within the electronic controller modules 97 along with the controller circuitry.

A wiring harness 101 (FIG. 6) is preferably provided for making electrical contact between the various electrical components in the prosthesis. The wiring harness 101 comprises a flat ribbon 102 of flexible material, such as a ribbon of flexible polymeric material, having conductor paths 103 formed along the surface of the ribbon 102 of flexible material. The conductor paths 103 terminate in mutually corresponding contact pads 104 adjacent various edges of the harness 101. The electrical conductors are of the printed circuit type, and the flexible material upon which the conductors are supported results in a highly reliable system with extended flexion life.

Figure 6:
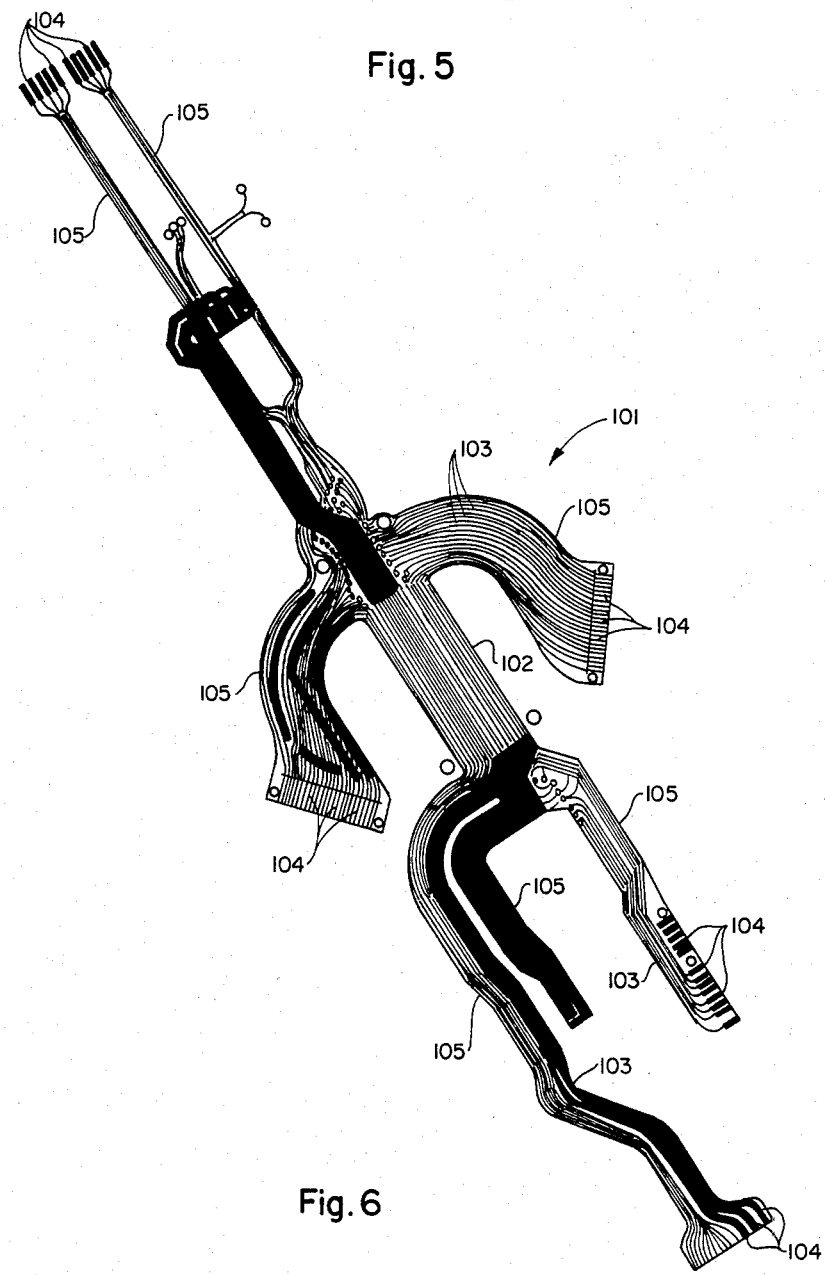
FIG. 6 is a pictorial view of a novel wiring harness used in the prosthesis of FIG. 1.

The harness 101 extends basically longitudinally through the forearm module 41 to the elbow module 23. The harness 101 thus preferably comprises an elongate central portion and a plurality of ribbon-like extensions 105, with the conductor paths extending from the central portion to corresponding extension 105 and with the contact pads 104 for the respective conductor paths 103 being positioned at the terminal and portions of the extensions 105. In the harness 101 as shown in FIG. 6, the larger central extensions are adapted to fit within the elbow module 23 and to be connected to the electronic controller modules 97 which basically contain all the electronic components of the prosthesis. The upper extensions as shown in FIG. 6 are adapted to extend through applicable opening in the flat upper end 25 of the elbow module 23 and the annular fitting 28 in the outer socket member 20 for connection to the skin electrode assemblies 91. Additional connections are made on the upper extensions as shown in FIG. 6 for the contacts which connect the battery pack module 98 to the system and for contact to the motor 57 of the locking mechanism in the elbow module 23. The lower extensions as shown in FIG. 6 are adapted to be connected to the motorized drive module 60 and supportive electronics mounted within the open framework portion of the forearm module 41, such as the potentiometers 93 and tachometer 95.

Figure 7:
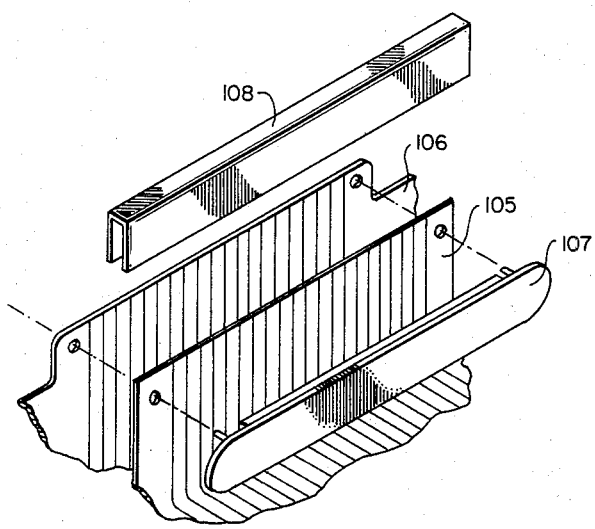
FIG. 7 is a partial pictorial showing a novel connector system used in the prosthesis of FIG. 1 to connect various components to the wiring harness.
Figure 8:
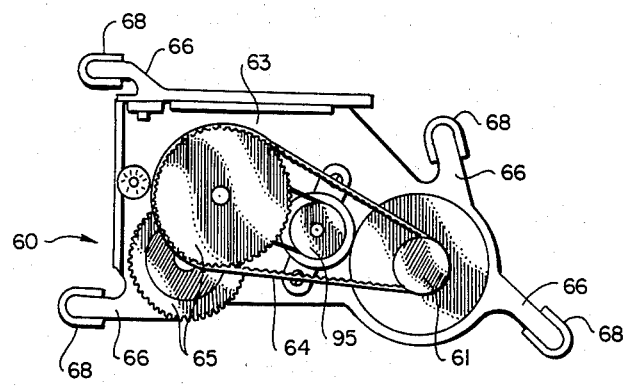
FIG. 8 is a back side view of the motor drive component of the prosthesis of FIG. 1.

Means are provided as illustrated in FIG. 7, for connecting the electrical leads from the electrical components to corresponding contact pads on the harness 101. The leads from the electrical components terminate in contact pads which are positioned on a substantially flat support member 106. The contact pads on the terminal end portions of the extensions 105 of the harness are releasably connected in electrical contact with the pads on the mutually respective support members 106 by means of a novel clip assembly. This clip assembly includes an elongate strip 107 of resilient material which is positioned along a respective side edge face of the terminal end portion of an extension 105 of the harness and/or the side face of the flat support member 106. As illustrated in FIG. 7 only one elongate strip 107 is used and it is shown positioned along the side edge face of the terminal end portion of an extension 105 of the harness. It is to be understood, however, that the elongate strip 107 could be positioned along the side edge face of the support member 106 or two such strips 107 could be used so that the strips 107 would be positioned along mutually respective sides of both the extension 105 and the support member 106.

Mutually respective extensions 105 and the support members 106 are positioned in side-by-side relationship with the contact pads on each member abutting corresponding pads on the other member. An elongate clip member 108 is provided to slip firmly over the strip 107 of resilient material and the extension 105 and support member 106. The resilient nature of the strip 107 results in a uniform force being applied to the clip member 108 to assure reliable, firm electrical contact between the pads of the respective extension 105 and the support member 106. In a minor variation, the strip of resilient material can be mounted on a flat shoe or backup member made of plastic. The resilient material still makes contact with the extension 105 and/or the support member 106, with the clip member 108 clipping firmly over the shoe or backup member. The solderless electrical connections made by the clip/compression system of this invention can be connected and disconnected easily, and the connections are extremely durable and reliable.

As can be seen from the above description of the preferred embodiments of the invention, the prosthesis comprises interconnectable, readily disconnected modules for wrist articulation, elbow flexion and humeral rotation. In addition, easily replaceable, internal modules are provided for actuators, electronics and drive systems. The modular nature of the prosthesis is extremely advantageous in increasing the operational availability of the prosthesis to amputees, since malfunctioning modules can readily be identified, isolated, and exchanged in the field. The malfunctioning modules can then be repaired at a central repair facility. Furthermore, improvements or modifications which are made to the prosthesis from time to time can be easily integrated in the field by a simple exchange of the appropriate module.

The structural modules which replace the missing arm and elbow structures and joints are designed to be exoskelatal for maximum strength as well as for providing protection for the internal components and modules. The external structures have further been designed to be readily disassembled or otherwise provide ready access to the internal components and modules. All major, exoskelatal, structural components are preferably made of injection molded nylon filled with up to 45% to 50% fiberglass or graphite fibers.

Although a preferred embodiment of the invention has been illustrated, it is to be understood that the present disclosure is made by way of example and that various modifications are possible without departing from the subject matter coming within the scope of the following claims, which subject matter we regard as our invention.

We claim:

1. A prosthesis for a person with an amputation above the elbow, to provide a replacement for at least the lower arm and elbow of the person, with the prothesis being made from internal and external modules which are readily replaceable, said prosthesis comprising:
    an upper arm or socket module which is adapted to be attached to the stump or shoulder portion of the person's torso;
    skin electrodes for monitoring the electromyographic signals from two antagonist muscles on the stump or torso of the person;
    an elbow module having a hollow cavity therewithin, with a locking pin member mounted within the hollow cavity and an opening in the elbow module through which the locking pin is adapted to move, said elbow module further including means for moving the locking pin back and forth in the opening in the elbow module between an extended position in which the end of the locking pin extends outwardly from said opening in the elbow module and a retracted position in which the end of the locking pin is retracted so as to not extend outwardly from said opening;
    means for connecting the elbow module to the socket module so that the elbow module can be rotated relative to the socket module about the longitudinal axis of the socket module;
    a forearm module comprising a hinged member adapted to be pivotally attached to the elbow module, said hinged member having an enclosed hollow back portion and a forward portion formed of a substantially open framework, said forearm module further comprising an elongate forearm cover member which is open at both of its ends and is adapted to slide over the framework portion of the hinged member for attachment to the framework portion, with the rear end of the forearm cover abutting the enclosed back portion of the hinged member such that the combined cover member and hinged member have the general shape of a human forearm, said hinged member being open at its end adjacent to the hollow back portion thereof so that the elbow module can be received within the hollow back portion of the hinged member when the hinged member is pivoted about its attachment to the elbow module, said hinged member also having attached firmly to an inside surface of the hollow back portion thereof a curved elongate lock member which has a plurality of detent holes equally spaced along the length thereof, said lock member being positioned along the inside surface of the hinged member so that as the hinged member pivots about its attachment to the elbow module, the curved elongate lock member moves in an arc such that the detent holes therein move successively back and forth directly beneath the opening in the elbow module, whereby the hinged member, and thus the forearm module, can be locked in place with respect to the elbow module at various positions in the movement of the forearm module relative to the elbow module by activating the lock pin to extend from the opening in the elbow module to engage one of the detent holes in the lock member;
    a motorized drive module for imparting pivotal movement of the forearm module relative to the elbow module, said drive module comprising a DC motor and gear reduction transmission mounted on a frame which is adapted to be removablyattached to the hinged member within the open framework of the hinged member, said drive module further including linkage means connected at one end thereof to the elbow module and at the other end thereof to the transmission, whereby the rotary motion of the motor is transmitted to substantially translational movement of the linkage which in turn imparts pivotal movement of the forearm module relative to the elbow module;
    a wrist module attached to the forward end of the forearm cover, said wrist module being adapted to have a hook or simulated hand removably attached thereto, said wrist module further including means for rotating the hook or simulated hand relative to the forearm about the longitudinal axis of the forearm;
    an electronic controller module adapted to receive the electromyographic signals from the skin electrodes to operate the DC motor of the motorized drive module; and
    a battery pack module which is removably received within a receptacle in the prosthesis so as to be connected to the electronic controller module for providing electrical power thereto.

2. A prosthesis as claimed in claim 1, wherein said elbow module has a substantially flat upper end and further wherein said means for connecting the elbow module to the socket module comprises:
    an annular fitting which is adapted to be attached to the end of the socket module, said annular fitting having a cylindrical end portion which extends away from the socket module and which has a substantially flat, circular end face, said cylindrical end portion being substantially coaxial with the longitudinal axis of the socket module, said cylindrical end portion further having a circumferencial flange or ring adjacent to the flat, circular, end face thereof;

an annular friction band having an annular recess formed around the inside surface at one end portion thereof so that the annular recess is adapted to engage the circumferential flange on said annular fitting, with the other end portion of the friction band adapted for attachment to the upper end of the elbow module to hold the flat upper end of the elbow module in parallel, closely spaced relationship with the flat, circular end of the annular fitting; and an adjustable tension band adapted to encircle the friction band and to provide adjustable compression of the friction band, whereby the ease with which the elbow module can be rotated relative to the socket module can be adjusted incrementally between essentially free rotation and various degrees of restrained rotation by adjusting the tension band to increase or decrease the compression exerted by the tension band on the friction band.

3. A prosthesis as claimed in claim 1, wherein the electronic controller module is mounted within the hollow cavity within the elbow module, and a portion of the exterior of the elbow module is removable so as to provide access to the cavity.

4. A prosthesis as claimed in claim 3 wherein the battery pack module is mounted within the cavity in said elbow module, with the battery pack module being adapted to be removably received within the cavity through an open space in the elbow module, with the outer end of the battery pack module being adapted to form a continuous surface for the open space in the elbow module when the battery pack module is positioned within the cavity of the elbow module.

5. A prosthesis as claimed in claim 1, wherein a wiring harness is provided for making electrical contact between electrical components of the prosthesis, said wiring harness comprising a flat ribbon of flexible material having conductor paths formed along the surface of the ribbon of flexible material, said conductor paths terminating in mutually corresponding contact pads adjacent various edges of the harness, and means are provided for connecting the electrical leads from the electrical components to corresponding contact pads on the harness.

6. A prosthesis as claimed in claim 5, wherein the wiring harness comprises a central portion and a plurality of ribbon-like extensions, with the conductor paths extending from the central portion to corresponding extensions and with the contact pads for the respective conductor paths being positioned at the terminal end portions of the extensions.

7. A prosthesis as claimed in claim 5, wherein the leads from the electrical components terminate in contact pads which are positioned on a substantially flat support member, and the means for connecting the electrical leads from the electrical components to corresponding contact pads on the harness comprises:

an elongate strip of resilient material positioned along at least one of the respective side edges of said harness and said flat support member when the harness and flat support member are positioned in side-by-side relationship with the pads on the harness abutting corresponding pads on the flat surface member;

and an elongate clip member adapted to clip firmly over the srip of resilient material and the side edges of the harness and the flat support member, whereby the pads on the harness are held in firm electrical contact with correspondig pads on the flat support member.

8. A prosthesis as claimed in claim 1, wherein the means for moving the locking pin back and forth in the opening in the elbow module comprises:

a spring cantilevered at its one end to a rotatable base, with the other end of the spring being adapted to contact the locking pin;

means for rotating the rotatable base from a first position through an angle of about 180 degrees to a second position and vice versa about an axis coinciding with the attachment of the spring to the rotatable base, whereby when the rotatable base is in its said first position, the spring biases the locking pin to move longitudinally to its extended position and when the rotatable base is in its said second position, the spring biases the locking pin to move longitudinally to its retracted position.

9. A prosthesis as claimed in claim 8, wherein the means for rotating the rotatable base includes:

a second DC motor;

a gear mechanism connecting the second DC motor to the rotatable base; and means for operating the second DC motor.

10. A prosthesis as claimed in claim 9, wherein the means for operating the second DC motor comprises:

means for measuring the torque at the pivotal attachment of the forearm module to the elbow module;

means for measuring the rotational movement of the forearm module relative to the elbow module; and wherein the electronic controller module comprises circuitry means for operating the second motor to rotate the rotatable base to its said first position only when the rotational movement of the forearm module is substantially zero and simultaneously the torque is above a predetermined value for a specified time interval, said electronic controller module further having circuitry means for operating the second motor to rotate the rotatable base to its said second position when a predetermined succession of electromyographic signals are received from the skin electrodes.

11. A prosthesis as claimed in claim 10, wherein the means for measuring the torque comprises means adapted to measure the force exerted on the elbow module by the linkage means of the motorized drive module, and the means for measuring the rotational movement of the forearm module comprises means for monitoring operation of the DC motor of the motorized drive module.

12. A prosthesis as claimed in claim 10, wherein the means for measuring said torque comprises:

an elongate stress member attached at one end thereof to the elbow module so as to displaced from and substantially parallel to the pivot axis about which the forearm module is attached to the elbow module, with the other end of the stress member being attached to the linkage means of the motorized drive module; and a strain guage associated with the stress member to measure strain therein from the force exerted on the stress member by the linkage means, and wherein the means for monitoring operation of the DC motor of the motorized drive module comprises:

an electrical generator driven from the drive shaft of the DC motor, whereby when the DC motor is operating, an output current is produced by the electrical generator.

13. A prosthesis as claimed in claim 1, wherein the frame on which the DC motor and the gear reduction transmission of the motorized drive module are mounted has at least three spaced projections extending therefrom, and the sides of the framework of the hinged member of the forearm module have a number of slots corresponding to the number of the projections on said frame, with the slots being adapted to receive the respective projections on the frame to effect attachment of the frame to the framework of the hinged member, and with the slots further being provided with removable end covers which prevent the projections on the frame from being removed from the slots until the removable end covers are removed from the slots.

14. A prosthesis as claimed in claim 13, wherein the spaced projections have a covering of resilient material about the end portion thereof, whereby the resilient material is compressed between the projections and the slots when the projections are positioned within their corresponding slots.

15. A prosthesis as claimed in claim 1, wherein the wrist module comprises:

a substantially cylindrical attachment member having external threads at one end thereof, with the other end of the attachment member being adapted to be secured to the forward end of the forearm cover;

an insert member comprising a cylindrical body which is open at one end and has an end cap at the other end thereof, said cylindrical body having a raised band circumscribing the central portion thereof, with the diameter of the raised band being of such size that the insert member with the raised band is adapted to fit coaxially within the one end of the cylindrical attachment member, said end cap having a bore therethrough which is coaxial with the cylindrical body of the insert member and which is adapted to receive attachment means for a hook or similated hand for attachment to said cap member;

an elastomeric o-ring adapted to fit circumferentially around the cylindrical body of the insert member between the one end of the cylindrical body and the raised band on the cylindrical body;

abutment means in the interior of the cylindrical attachment member, said abutment means adapted to fit over the cylindrical body of the insert member and to abut the o-ring when said one end of the insert member is fit within the cylindrical attachment member such that the o-ring is constrained between the raised band on the cylindrical body and the abutment means as the insert member is moved toward the abutment means; and a screw ring adapted to be threaded on the external threads of the cylindrical attachment member and to advance the insert member toward the abutment means within the cylindrical attachment member as the screw ring is advanced on the threads of the cylindrical attachment member, thereby compressing the o-ring between the abutment member, the raised ring, the cylindrical body of the insert member, and the interior surface of the cylindrical attachment member to progressively inhibit rotational movement of the insert member relative to the attachment member as the screw ring is advanced on the threads of the cylindrical attachment member.

16. A prosthesis as claimed in claim 15, wherein the abutment means comprises:

an internal circumferential lip on the inside surface of the cylindrical attachment member and spaced from said one end thereof;

at least one longitudinal keyway in the cylindrical attachment member, said keyway extending from said one end of the cylindrical attachment member substantially to the lip on the inside surface of the cylindrical attachment member;

a bearing ring made of a polymeric material and adapted to fit within the cylindrical attachment member, with one end of the bearing ring abutting the lip on the inside surface of the cylindrical attachment member, said bearing ring also having a number of keys equal to the number of keyways in the cylindrical attachment member, with said keys, which extend from the outer periphery of the bearing ring, being adapted to be received in the corresponding keyways in the cylindrical attachment member.

whereby the other end of the bearing ring abuts said o-ring when the o-ring and insert member are positioned in the cylindrical attachment member.

17. A prosthesis as claimed in claim 16, wherein a second bearing ring made of polymeric material is adapted to fit between the insert member and the screw ring so that the screw ring presses against the second bearing ring and the second bearing ring in turn presses against the insert member when the screw ring is advanced on the threads of the cylindrical attachment member.

18. A prosthesis as claimed in claim 15, wherein the bore through the end cap of the insert member is threaded so as to be adapted to receive a threaded stud of a hook or simulated hand.

19. A prosthesis as claimed in claim 1, wherein the electronic controller module is adapted to operate the DC motor of the drive module over a range of speeds corresponding to the values of the electromyographic signals received from the skin electrodes, and circuitry means are provided for adjusting the sensitivity of the response of the electronic controller to the electromyographic signals received from the skin electrodes.

20. In a prosthesis for a person with an amputation above the elbow, said prosthesis including an upper arm socket which is adapted to be attched to the stump or shoulder portion of the person's torso and an elbow and forearm section attached to said upper arm socket, an improved connection means between the upper arm socket and the elbow section which provides humeral rotation, said improved connection means comprising:

an annular fitting which is adapted to be attached to the end of the upper arm socket, said annular fitting having a cylindrical end portion which extends away from the upper arm socket and which as a substantially flat, circular end face, said cylindrical end portion being substantially coaxial with the longitudinal axis of the upper arm socket, said cylindrical end portion further having a circumferential flange or ring adjacent to the flat, circular end face thereof;

providing the elbow section with a substantially flat upper end;

an annular friction band having an annular recess formed around the inside surface at one end portion thereof so that the annular recess is adapted to engage the circumferential flange on said annular fitting, with the other end portion of the friction band adapted for attachment to the upper end of the elbow section to hold the flat upper end of the elbow section in parallel closely spaced relationship with the flat, circular end of the annular fitting; and an adjustable tension band adapted to encircle the friction band and to provide adjustable compression of the friction band, whereby the ease with which the elbow section can be rotated relative to the upper arm socket can be adjusted incrementally between essentially free rotation and various degrees of restrained rotation by adjusting the tension band to increase or decrease the compression exerted by the tension band on the friction band.

21. In a prosthesis for a person with a amputation above the elbow, said prosthesis including an upper arm socket which is adapted to be attached to the stump or shoulder portion of the person's torso, an elbow member attached to the upper arm socket and a forearm member hingedly attached to the elbow member, an improvement comprising means for locking the forearm member in place with respect to the elbow member, said improvement comprising:

a locking pin member mounted within a hollow cavity in the elbow member, with an opening in the elbow member through which the locking pin is adapted to move;

means for moving the locking pin back and forth in the opening in the elbow member between an extended position in which the end of the locking pin extends outwardly from said opening in the elbow member and a retracted position in which the end of the locking pin is retracted so as to not extend outwardly from said opening;

said forearm member having an enclosed hollow end portion which is pivotally attached to the elbow member, with an opening being provided in said hollow end portion of the forearm so that the elbow member is received within the hollow end portion of the forearm member when the forearm member is pivoted about its attachment to the elbow member, said forearm member also having attached firmly to an inside surface of the hollow end portion thereof a curved, elongate, lock member which has a plurality of detent holes equally spaced along the length thereof, said lock member being positioned along said inside surface so that as the forearm member pivots about its attachment to the elbow member, the curved, elongate, lock member moves in an arc such that the detent holes therein move successively back and forth directly beneath the opening in the elbow member through which the locking pin is adapted to move, whereby the forearm member can be locked in place with respect to the elbow member at various positions in the pivotal movement of the forearm member relative to the elbow member by activating the lock pin to extend from the opening in the elbow member to engage one of the detent holes in the lock member.

22. A prosthesis as claimed in claim 21, wherein the means for moving the locking pin back and forth in reciprocating motion in the opening in the elbow member comprises:

a spring cantilevered at its one end to a rotatable base, with the other end of the spring being adapted to contact the locking pin;

means for rotating the rotatable base from a first position through an angle of about 180 degrees to a second position and vice versa about an axis coinciding with the attachment of the spring to the rotatable base, whereby when the rotatable base is in its firsrt position, the spring biases the locking pin to move longitudinally to its extended position and when the rotatable base is in its said second position, the spring biases the locking pin to move longitudinally to its retracted position.

23. A prosthesis as claimed in claim 22, wherein said means for rotating said rotatable base comprises:

a DC motor;

a gear mechanism connecting the DC motor to the rotatable base; and means for operating the DC motor.

24. A prosthesis as claimed in claim 23, wherein the means for operating the DC motor comprises:

means for measuring the torque at the pivotal attachment of the forearm member to the elbow member;

means for measuring the rotational movement of the forearm member relative to the elbow member; and electronic controller means including circuitry means for operating the DC motor to rotate the rotatable base to its said first position only when the rotational movement of the forearm member is substantially zero and simultaneously the torque is above a predetermined value for a specific time interval, said electronic controller means further having circuitry means for operating the DC motor to rotate the rotatable base to its said second position when a predetermined command is given by the person wearing the prosthesis.

25. In a prosthesis for a person with an amputation above the wrist, said prosthesis including a forearm member and a hook or simulated hand, an improved means simulating a wrist, said improved means comprising:

a substantially cylindrical attachment member having external threads at one end thereof, with the other end of the attachment member being adapted to be secured to the forward end of the forearm member;

an insert member comprising a cylindrical body which is open at one end and has an end cap at the other end thereof, said cylindrical body having a raised band circumscribing the central portion thereof, with the diameter of the raised band being of such size that the insert member with the raised band is adapted to fit coaxially within the one end of the cylindrical attachment member, said end cap having a bore therethrough which is coaxial with the cylindrical body of the insert member and which is adapted to receive attachment means for a hook or simulated hand for attachment to said cap member;

an elastomeric o-ring adapted to fit circumferentially around the cylindrical body of the insert member between the one end of the cylindrical body and the raised band on the cylindrical body;

abutment means in the interior of the cylindrical attachment member, said abutment means adapted to fit over the cylindrical body of the insert member and to abut the o-ring when said one end of the insert member is fit within the cylindrical attachment member such that the o-ring is constrained between the raised band on the cylindrical body and the abutment means as the insert member is moved toward the abutment means; and a screw ring adapted to be threaded on the external threads of the cylindrical attachment member and to advance the insert member toward the abutment means within the cylindrical attachment member as the scew ring is advanced on the threads of the cylindrical attachment member, thereby compressing the o-ring between the abutment member, the raised ring, the cylindrical body of the insert member, and the interior surface of the cylindrical attachment member to progressively inhibit rotational movement of the insert member relative to the attachment member as the screw ring is advanced on the threads of the cylindrical attachment member.

26. A prosthesis as claimed in claim 25, wherein the abutment means comprises:

an internal circumferential lip on the inside surface of the cylindrical attachment member and spaced from said one end thereof;

at least one longitudinal keyway in the cylindrical attachment member, said keyway extending from said one end of the cylindrical attachment member substantially to the lip on the inside surface of the cylindrical attachment member;

a bearing ring made of a polymeric material and adapted to fit within the cylindrical attachment member, with one end of the bearing ring abutting the lip on the inside surface of the cylindrical attachment member, said bearing ring also having a number of keys equal to the number of keyways in the cylindrical attachment member, with said keys, which extend from the outer periphery of the bearing ring, being adapted to be received in the corresponding keyways in the cylindrical attachment member, whereby the other end of the bearing ring abuts said o-ring when the o-ring and insert member are positioned in the cylindrical attachment member.

27. A prosthesis as claimed in claim 26, wherein a second bearing ring made of polymeric material is adapted to fit between the insert member and the screw ring so that the screw ring presses against the second bearing ring and the second bearing ring in turn presses against the insert member when the screw ring is advanced on the threads of the cylindrical attachment member.

28. A prosthesis as claimed in claim 25, wherein the bore through the end cap of the insert member is threaded so as to be adapted to receive a threaded stud of a hook or simulated hand.

* * * * *